US008953172B2

(12) United States Patent
Kawano et al.

(10) Patent No.: US 8,953,172 B2
(45) Date of Patent: Feb. 10, 2015

(54) OPTICAL COHERENCE TOMOGRAPHY OBSERVATION APPARATUS, METHOD FOR DETERMINING RELATIVE POSITION OF IMAGES, AND PROGRAM FOR DETERMINING RELATIVE POSITION OF IMAGES

(71) Applicant: Nikon Corporation, Tokyo (JP)

(72) Inventors: Takeshi Kawano, Tokyo (JP); Shigeru Nakayama, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 14/031,729

(22) Filed: Sep. 19, 2013

(65) Prior Publication Data

US 2014/0016136 A1  Jan. 16, 2014

Related U.S. Application Data

(63) Continuation of application No. PCT/JP2012/057615, filed on Mar. 23, 2012.

(30) Foreign Application Priority Data

Mar. 24, 2011 (JP) .................................. 2011-066744

(51) Int. Cl.
*G01B 11/02* (2006.01)
*G01B 9/02* (2006.01)
(Continued)

(52) U.S. Cl.
CPC ........ *G01B 9/02091* (2013.01); *G01N 21/4795* (2013.01); *G01B 9/02044* (2013.01); *G01B 9/02087* (2013.01); *G01N 2021/1787* (2013.01)
USPC ........................................................ 356/497

(58) Field of Classification Search
USPC ................. 356/479, 497; 250/227.19, 227.27
See application file for complete search history.

(56) References Cited

U.S. PATENT DOCUMENTS

| 7,236,251 B2* | 6/2007 | Takaoka ........................ 356/497 |
| 7,872,759 B2* | 1/2011 | Tearney et al. ............... 356/479 |
| 8,204,300 B2 | 6/2012 | Sugita et al. |
| 2006/0181791 A1* | 8/2006 | Van Beek et al. ............. 359/845 |

(Continued)

FOREIGN PATENT DOCUMENTS

| JP | 2012/510531 A | 3/2009 |
| WO | WO 2007/057615 | 4/2007 |

OTHER PUBLICATIONS

Aguirre, Aaron D. et al. "Cellular resolution ex vivo imaging of gastrointestinal tissues with optical coherence microscopy". Journal of Biomedical Optics, vol. 15(1), Jan./Feb. 2010, pp. 016025-1-016025-9.*

(Continued)

*Primary Examiner* — Michael A Lyons
(74) *Attorney, Agent, or Firm* — Finnegan, Henderson, Farabow, Garrett & Dunner, L.L.P.

(57) ABSTRACT

An optical coherence tomography observation apparatus comprising a controller (30) and a detector (40), the controller being configured to illuminate first illumination light to an observation object, cause an image generator to generate a first tomographic image showing tomography of the observation object, illuminate second illumination light to the observation object, and cause the image generator to generate a second tomographic image showing tomography of the observation, and the detector being configured to detect a relative position of the second tomographic image with respect to the first tomographic image, at which a correlation of the second tomographic image with the first tomographic image becomes highest, are provided.

15 Claims, 9 Drawing Sheets

(51) Int. Cl.
*G01N 21/47* (2006.01)
*G01N 21/17* (2006.01)

(56) References Cited

U.S. PATENT DOCUMENTS

2007/0229801 A1 10/2007 Tearney et al.
2012/0044456 A1* 2/2012 Hayashi ........................ 351/206

OTHER PUBLICATIONS

Written Opinion of the International Searching Authority issued by the Japanese Patent Office in International Application No. PCT/JP2012/057615, mailed Jul. 3, 2012 (8 pages).

International Search Report issued by the Japanese Patent Office in international Application No. PCT/JP2012/057615, mailed Jul. 3, 2012 (4 pages).

Y. Yasuno, et al., "Non-iterative numerical method for laterally super-resolving Fouier domain optical coherence tomography", Optics Express. vol. 14, No. 3 (Feb. 6, 2006) pp. 1006-1020.

D. Huang, et al., "Optical Coherence Tomography", Science, New Series, vol. 254, No. 5035 (Nov. 22, 1991) pp. 1178-1181.

W. Drexler, et al., "In Vivo ultrahigh-resolution optical coherence tomography". Optics Letters, vol. 24, No. 17 (Sep. 1, 1999) pp. 1221-1223.

* cited by examiner

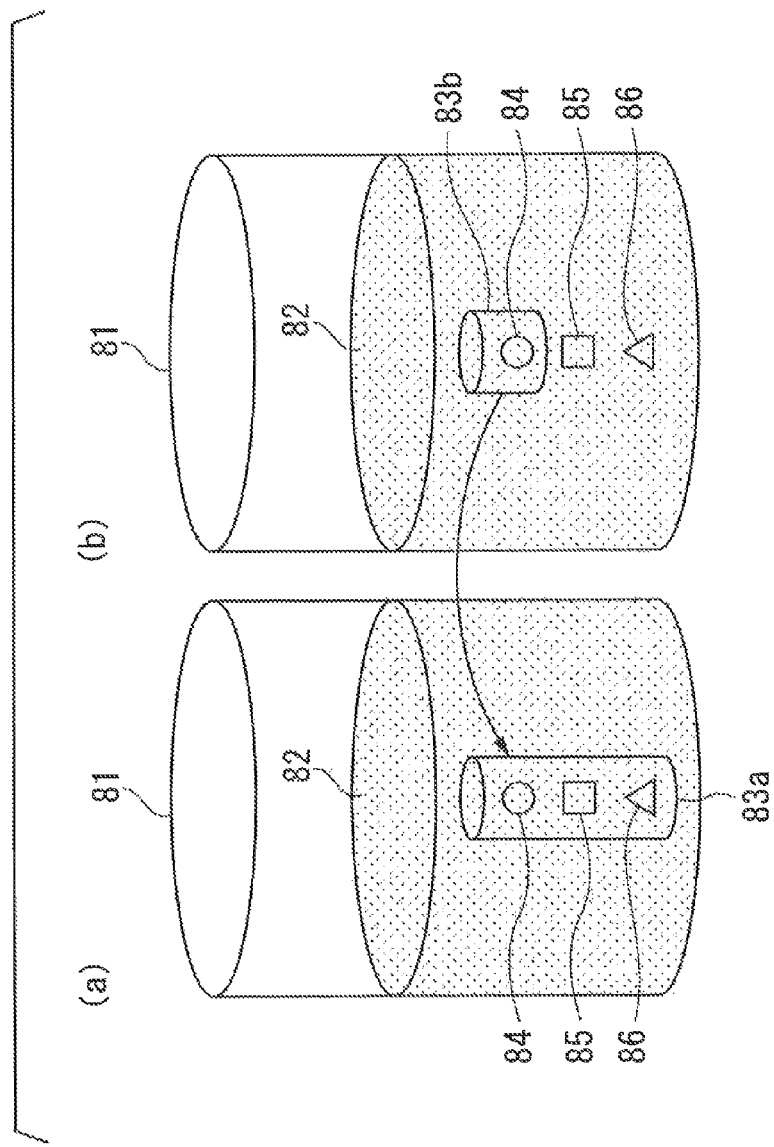

OPTICAL COHERENCE TOMOGRAPHY OBSERVATION APPARATUS, METHOD FOR DETERMINING RELATIVE POSITION OF IMAGES, AND PROGRAM FOR DETERMINING RELATIVE POSITION OF IMAGES

CROSS-REFERENCE TO RELATED APPLICATION

This is a Continuation application of International Application No. PCT/JP2012/057615, filed Mar. 23, 2012, which claims priority to Japanese Patent Application No. 2011-066744 filed on Mar. 24, 2011. The contents of the aforementioned applications are incorporated herein by reference.

BACKGROUND

1. Field of the Invention

The present invention relates to an optical coherence tomography observation apparatus, a method for determining a relative position of images, and a program for determining the relative position of images.

2. Description of Related Art

Generally, in cell culture of the related art, cells which are two-dimensionally grown are observed, and the properties are evaluated. However, in order to express essential properties of the cells, the importance of growing the cells three-dimensionally has been becoming clear in recent years.

With the above-described background, expectations with respect to a method which observes three-dimensional structures of the cells have increased.

Optical Coherence tomography (OCT) which uses low coherence light has advantages such as a resolution on the order of μm in a depth direction and an observation range on the order of mm in the depth direction, and is a promising technology which observes three-dimensional structures of cells (Non-Patent Document 1).

Research and development of OCT has advanced since the 1990s, and OCT is generally divided into two kinds of OCTs such as a time domain method and Fourier domain method.

In the OCT of the time domain method, a light beam is divided into signal light and reference light, the signal light scattered from cells and the reference light reflected from a reference mirror become interfere with each other, and interference light is generated. At this time, since coherency of the light beam used in a light source is low, only the signal light from a specific depth which is scattered from the cells becomes interfere with the reference light. Accordingly, the depths of the cells exhibiting the interference can be changed by changing the light path length of the reference light, and three-dimensional structures of the cells can be observed.

However, in the OCT of the time domain method, since information in the depth direction is obtained by moving the reference mirror in an optical axis direction, the measurement time is long, and thus, currently, the OCT of the time domain method has not been adopted. On the other hand, in the OCT of the Fourier domain method, since the information in the depth direction can be collectively obtained, the measurement time is short, and thus, currently, the OCT of the Fourier domain method has become a mainstream method (Non-Patent Document 2).

Here, the OCT of a spectrum domain method (SD-OCT) which is a kind of OCT of the Fourier domain method is described as an example. In the SD-OCT, the observation range in the depth direction is limited by the spectral resolution of a spectroscope and the focal depth of an objective lens.

For example, it is assumed that the observation range in the depth direction determined by the spectral resolution of the spectroscope is the same as the observation range in the depth direction determined by the focal depth of the objective lens. When the observation range in the depth direction is widened by increasing the spectrum resolution, the focal depth of the objective lens also needs to be deep. In order to make the focal depth of the objective lens deep, the numerical aperture (NA) of the objective lens needs to be decreased. However, since lateral resolution (the resolution in a horizontal direction) is inversely proportional to the NA of the objective lens, the lateral resolution (the resolution in the horizontal direction) necessarily decreases if the NA is decreased.

Conversely, when the observation range in the depth direction is narrowed by the decreasing of the spectrum resolution, the observation can be performed with high lateral resolution using an objective lens having a shallow focal depth and a large NA. That is, the observation range in the depth direction and the lateral resolution are in a trade-off relationship.

From the above-described relationships, in order to widen the observation range in the depth direction in a state where the lateral resolution is maintained, generally, a method is adopted in which tomographic images (hereinafter, referred to as "OCT images") having narrow observation ranges in the depth direction are obtained in plural sheets and the plurality of sheets of the tomographic images are connected to each other Non-Patent Document 3).

RELATED ART DOCUMENTS

Non-Patent Documents

[Non-Patent Document 1]D. huang, E A Swanson, c P Lin, J S Schuman, W G Stinson, W Chang, M R Hee, t Flotte, K Gragory, C A Puliafito and et. al, "Optical coherence tomography" Science Vol. 254, No. 5035, 1178-1181, 1991

[Non-Patent Document 2]Y. Yasuno, J. Sugisaka, Y. Sando, Y. Nakamura, S. Makita, M. Itoh and T. Yatagai, "Non-interactive numerical method for laterally superresolving Fourier domain optical coherence tomography" Optical Express Vol. 14, Iss. 3, 1006-1020, 2006

[Non-Patent Document 3]W. Drexler, U. Morgner, F. X. Kartner, S. A. Boppart, X. D. Li, E. P. Ippen, and J. GFujimoto, "In vivo ultrahigh-resolution optical coherence tomography" OPTICS LETTERS Vol. 24, No. 17, 1221-1223, 1999

SUMMARY

In the optical coherence tomography observation apparatus of the related art, when the plurality of sheets of OCT images are connected to each other in the depth direction, if the OCT images having narrow observation ranges in the depth direction are obtained at equal intervals in the depth direction and the OCT images can be simply connected to each other, the OCT images having wide observation ranges in the depth direction can be easily formed. In order to perform the process, it is assumed that the position of a stage or an optical system which holds a biological sample can correctly move at equal intervals in the depth direction. Moreover, it is also assumed that the position in the lateral direction does not deviate.

However, in the optical coherence tomography observation apparatus, it is difficult to correctly move the position of the stage holding the biological sample or the optical system at equal intervals in the depth direction and to move the position of the stage or the optical system in the lateral direction without deviation of the position.

Moreover, when accuracy of a position control of the stage or the optical system is insufficient in the first place compared to the resolution of the optical system, there is a problem that the optical coherence tomography observation apparatus cannot correctly move the stage or the optical system.

Accordingly, the aspects of the present invention provide a technology which can generate a tomographic image having a wide observation range from a tomographic image having a narrow observation range.

According to an aspect of the present invention, there is provided an optical coherence tomography observation apparatus, including: a splitting device that is configured to split incident light into reference light and illumination light, an illumination optical system that is configured to illuminate an observation object by the illumination light, an observation optical system that is configured to observe light from the observation object obtained by illuminating the illumination light and forms an image, a combining device that is configured to make the reference light and the measurement light interfere with each other, and a light detection unit that is configured to detect interference light obtained from the interference by the combining device, a light control unit that is configured to change a plurality of numerical apertures, at least one optical system of the illumination optical system and the observation optical system having the light control unit, an image generator that is configured to generate a first tomographic image of the observation object based on first interference light and to generate a second tomographic image of the observation object based on second interference light, the first interference light being detected by the light detection unit in a state where the light control unit is set to a first numerical aperture, the second interference light being detected by the light detection unit in a state where the light control unit is set to a second numerical aperture different from the first numerical aperture, and a detector that is configured to detect a relative position of the second tomographic image generated by the image generator with respect to the first tomographic image generated by the image generator, at which a correlation of the second tomographic image with the first tomographic image becomes highest.

According to another aspect of the present invention, there is provided a method for determining relative position of images which is performed by an optical coherence tomography observation apparatus which includes a light detection unit detecting interference light and light control unit for changing a plurality of numerical apertures, the method including: an image generation process of generating a first tomographic image of the observation object based on first interference light and generating a second tomographic image of the observation object based on second interference light, the first interference light being detected by the light detection unit in a state where the light control unit sets a first numerical aperture, the second interference light being detected by the light detection unit in a state where the light control unit sets a second numerical aperture different from the first numerical aperture, and a detection process of detecting a relative position of the second tomographic image with respect to the first tomographic image, at which an correlation of the second tomographic image with the first tomographic image becomes highest.

According to still another aspect of the present invention, there is provided a program for determining relative position of images, causing a computer, which includes a storage unit in which information indicating a first tomographic image and a second tomographic image which show tomography of an observation object is stored, to execute: a detection step of reading the information indicating the first tomographic image and the information indicating the second tomographic image from the storage unit, and detecting a relative position of the second tomographic image with respect to the first tomographic image, at which a correlation of the second tomographic image with the first tomographic image becomes highest.

According to the aspects of the present invention, even when the stage or the optical system in not correctly moved, a tomographic image having a wide observation range can be generated from a tomographic image having a narrow observation range.

BRIEF DESCRIPTION OF THE DRAWINGS

FIG. 2 is a diagram in which an observation range of a first tomographic image which is obtained using a first objective lens having a low NA and an observation range of a second tomographic image which is obtained using a second objective lens having a high NA are shown.

DESCRIPTION OF EMBODIMENTS

Hereinafter, embodiments of the present invention will be described in detail with reference to the drawings. In the embodiments of the present invention, in OCTs of the Fourier domain method, OCT of a spectrum domain method (SD-OCT) will be described as an example.

Figure 1:
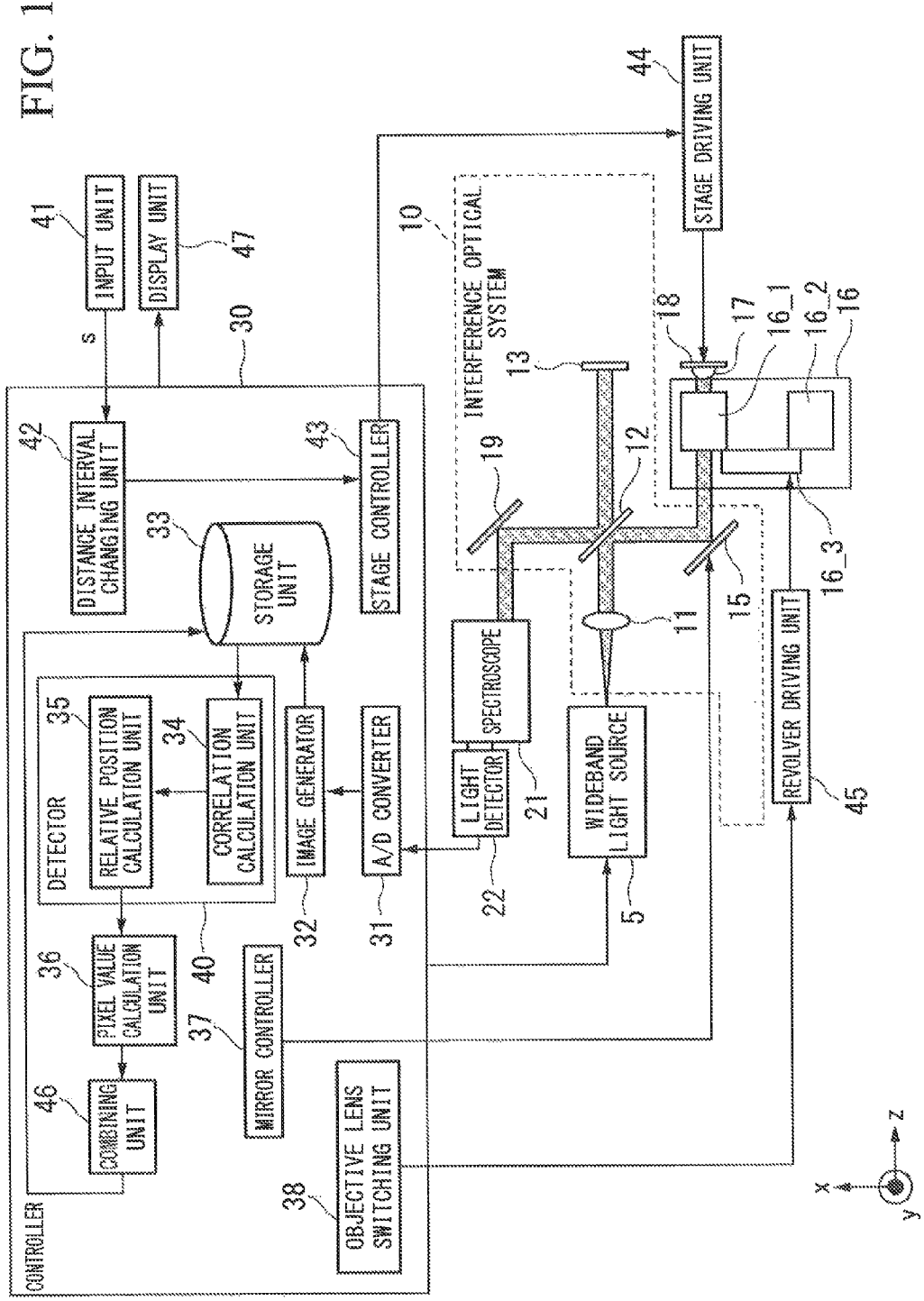
FIG. 1 is a functional block diagram of an optical coherence tomography observation apparatus according to a first embodiment.

FIG. 1 is a functional block diagram of an optical coherence tomography observation apparatus 1 according to a first embodiment. The optical coherence tomography observation apparatus 1 includes a wideband light source (a light source) 5, an interference optical system 10, an objective lens unit 16, a stage 18, a spectroscope 21, a light detector (light detection unit) 22, a controller 30, an input unit 41, a stage driving unit 44, a revolver driving unit 45 (light control unit, switching unit, and selection unit), and a display unit 47.

Here, a biological sample, which is an example of an observation object which becomes an object from which a tomographic image is obtained, is grown in a culture medium in a Petri dish (not shown), and the Petri dish is fixed onto the stage 18.

The biological sample is spread in x, y, and z directions, and the optical coherence tomography observation apparatus 1 photographs the tomographic image in the z direction which is a depth direction of the biological sample.

Moreover, the interference optical system 10 includes a condensing lens 11, a beam splitter 12, a reference mirror 13, a galvanomirror 15, an objective lens unit 16, and a mirror 19.

The interference optical system 10 includes a function as an illumination optical system which illuminates an observation object by illumination light, and a function as an observation optical system which observes the light from the observation object obtained by illuminating the illumination light and forms an image.

The objective lens unit 16 includes a first objective lens 16_1, a second objective lens 16_2, and a revolver 16_3. The first objective lens 16_1 and the second objective lens 16_2 are mounted on the revolver 16_3. The revolver 16_3 is rotatable, and the first objective lens 16_1 and the second objective lens 16_2 are switched from each other by rotating the revolver 16_3.

Moreover, the controller 30 includes an A/D converter 31, an image generator 32, a storage unit 33, a detector 40, a pixel value calculation unit 36, a combining unit 46, a mirror controller 37, an objective lens switching unit 38 (light control unit), a distance interval changing unit 42, and a stage controller 43. Here, the detector 40 includes a correlation calculation unit 34 and a relative position calculation unit 35.

An outline of the optical coherence tomography observation apparatus 1 according to the present embodiment will be described with reference to FIG. 2. FIG. 2 is a diagram in which an observation range of a first tomographic image which is obtained using the first objective lens 16_1 having a low NA and an observation range of a second tomographic image which is obtained using the second objective lens 16_2 having a high NA are shown.

FIG. 2(*a*) is a diagram in which the observation range of the first tomographic image which is obtained using the first objective lens 16_1 having a low NA (that is, the observation range is wide) is shown. FIG. 2(*a*) shows that a first cell 84, a second cell 85, and a third cell 86 are grown in a culture medium 82 of a Petri dish 81. In the drawing, in order to classify each cell, the first cell 84, the second cell 85, and the third cell 86 are drawn by a circle, a square, and a triangle respectively. Moreover, the first cell 84, the second cell 85, and the third cell 86 may be the cell of the same kind. In addition, an observation range 83*a* of the first tomographic image shows a range which includes all three cells described above.

FIG. 2(*b*) is a diagram in which an observation range of a second tomographic image which is obtained using the second objective lens 16_2 having a high NA (that is, the observation range is narrow) is shown. All biological samples of FIG. 2(*b*) are the same as the biological samples of FIG. 2(*a*). That is, the first cell 84, the second cell 85, and the third cell 86 which are the same biological samples as those of FIG. 2(*a*) are grown in the Petri dish 81 and the culture medium 82 which are the same as those of FIG. 2(*a*). However, an observation range 83*b* of the second tomographic image is narrower than the observation range 83*a* of the first tomographic image, and here, is a range which includes only the first cell. Accordingly, as shown by an arrow in FIG. 2, the observation range 83*b* of the second tomographic image corresponds to a range which includes the first cell 84 in the observation range 83*a* of the first tomographic range.

The optical coherence tomography observation apparatus 1 obtains the first tomographic image using the first objective lens 16_1. The optical coherence tomography observation apparatus 1 obtains the second tomographic image so that the second tomographic images are partially overlapped using the second objective lens 16_2 which has a higher NA than that of the first objective lens 16_1. In addition, in a relative position of the second tomographic image with respect to the first tomographic image, the optical coherence tomography observation apparatus 1 detects a relative position of the second tomographic image with respect to the first tomographic image, at which a correlation of the second tomographic image with the first tomographic image becomes highest.

The wideband light source 5 emits wideband light to the condensing lens 11 of the interference optical system 10. Here, for example, the wideband light is light which has a peak at a wavelength of 800 nm and a full width at half maximum of 200 nm, and a coherent length is short in the wideband light. For example, as the wideband light source (light source) 5, a super luminescent diode or the like is used.

The condensing lens 11 concentrates the light emitted from the wideband light source 5 so as to be the width of a predetermined light, and the concentrated light is guided to the beam splitter 12.

The beam splitter 12 includes a function as splitting device for dividing the emitted light into illumination light which is illuminated to the observation object and reference light which is illuminated to the reference mirror 13, and a function as optical combining device for generating interference light by combining the light from the observation object obtained by illuminating the illumination light to the observation object and the reflected reference light.

The beam splitter 12 having a function as a light division unit divides collimated light into the reference light and the illumination light, and the reference light and the illumination light are guided to the reference mirror 13 and the galvanomirror 15 respectively. That is, the beam splitter 12 divides the light emitted from the wideband light source 5 into the illumination light, which is illuminated to the observation object, and the reference light.

The reference mirror 13 reflects the reference light incident from the beam splitter 12 and guides the reflected reference light to return to the beam splitter 12.

The galvanomirror 15 is positioned at an exit pupil position of the objective lens which is used for the photographing of either the first objective lens 16_1 or the second objective lens 16_2. The galvanomirror 15 reflects the illumination light which is guided by the beam splitter 12 and guides the reflected light to the objective lens unit 16.

The mirror controller 37 controls the direction of the galvanomirror 15 so that the illumination light scans the biological sample in a horizontal direction which is perpendicular to the depth direction of the biological sample.

The direction of the galvanomirror 15 is changed by the control of the mirror controller 37. Accordingly, the galvanomirror 15 can cause the illumination light to scan in the horizontal direction (xy plane). Moreover, the galvanomirror 15 descans the illumination light which is reflected (also includes scattering) from the biological sample, and guides the light obtained by the descanning to the beam splitter 12.

The objective lens unit 16 includes the first objective lens 161, the second objective lens 16_2, and the revolver 16_3. The NA of the second objective lens 16_2 is larger than that of the first objective lens 16_1. Moreover, for simplification, the magnification of the first objective lens 16_1 is the same as that of the second objective lens 16_2.

Moreover, in the present embodiment, the magnification of the first objective lens 16_1 is the same as that of the second objective lens 16_2; however, the present invention is not limited to this, and the magnification of the first objective lens 16_1 may be different from that of the second objective lens 16_2.

The objective lens switching unit 38 outputs switching signals, which indicate to which of the first objective lens 16_1 and the second objective lens 16_2 the objective lens is switched, to the revolver driving unit 45. The revolver driving unit 45 supplies revolver driving signals, which drive the revolver 16_3 based on the switching signals output from the objective lens switching unit 38, to the revolver 16_3.

The revolver 16_3 makes the revolver 16_3 itself rotate based on the revolver driving signals supplied from the revolver driving unit 45, and switches the objective lens between the first objective lens 16_1 and the second objective lens 16_2.

The first objective lens 16_1 or the second objective lens 16_2 concentrate the illumination light to the biological sample 17 on the stage 18. In addition, the illumination light (hereinafter, referred to as "signal light") which is reflected (includes scattering) by the biological sample 17 is incident to the first objective lens 16_1 or the second objective lens 16_2. The incident signal light is guided to return to the beam splitter 12 via the galvanomirror 15.

The beam splitter 12 having a function as a light combining unit combines the signal light which is returned via the galvanomirror 15 and the reference light which is reflected by the reference mirror 13. The beam splitter 12 guides the interference light obtained by the combining to the spectroscope 21 via the mirror 19.

The spectroscope 21 spectrally resolves the interference light which is reflected by the mirror 19 and is incident, and supplies the spectrally resolved interference light to the light detector 22.

The light detector 22 detects the interference light which is spectrally resolved, and supplies signals, which indicate the luminance of the detected interference light, to the A/D converter 31. For example, the light detector 22 is a CCD image sensor.

The A/D converter 31 converts the signals, which indicate the luminance of the interference light supplied from the light detector 22, to digital signals, and supplies the converted digital signals to the image generator 32.

The image generator 32 performs the reverse Fourier transform to the digital signals which are supplied from the A/D converter 31, and obtains the information of the tomographic image in which the depth of the focal depth is present in the z direction at a focus spot in the xy plane which includes the biological sample 17. Signal light is scanned onto the biological sample by the galvanomirror 15 which is operated by the mirror controller 37, and thus, the image generator 32 obtains a three-dimensional tomographic image (OCT image). That is, the image generator 32 obtains a three-dimensional image which indicates the tomography of the observation object based on the light detected by the light detector 22. Moreover, the image generator 32 stores the data of the OCT image in the storage unit 33.

The controller 30 illuminates first illumination light, which is concentrated by the first objective lens 16_1, to the biological sample which is the observation object, and makes the image generator 32 obtain a first tomographic image which shows the tomography of the observation object. In addition, the controller 30 illuminates second illumination light, which is concentrated by the second objective lens 16_2, to the observation object, and makes the image generator 32 obtain a second tomographic image which shows the tomography of the observation object.

Here, generally, since the focal depth is inversely proportional to the square of the NA, in the objective lens, the larger is the NA, the narrower is the observation range. Accordingly, the image generator 32 can obtain the first tomographic image, and the second tomographic image in which the observation range in the depth direction is narrower than that of the first tomographic image.

The image generator 32 stores the data of the first tomographic image and the data of the second tomographic image in the storage unit 33. In addition, the controller 30 reads the data of the first tomographic image from the storage unit 33, and displays the data of the first tomographic image on the display unit 47.

The input unit 41 receives input of information which denotes definition s which indicates whether the OCT image is obtained in low definition or in high definition. The input unit 41 outputs the information, which indicates the received definition s, to the distance interval changing unit 42.

Based on the information (for example, information which indicates a high-definition mode and information which indicates a low-definition mode) which indicates the definition s, the distance interval changing unit 42 changes a distance interval when an optical relative position, which is a relative position of the biological sample which is the observation object and the interference optical system 10, is changed. Moreover, the distance interval changing unit 42 reduces the distance interval so that a wider region in which the second tomographic images are overlapped is obtained in the high-definition mode than in the low-definition mode. Since the image having high lateral resolution is obtained when the image is close to the focal position of the illumination light in the focal depth, higher definition of the tomographic image can be obtained in the high-definition mode than in the low-definition mode.

Specifically, for example, when the information which indicates the definition s is the information which indicates the low-definition mode, the distance interval changing unit 42 sets the distance interval, by which the stage moves each time the second tomographic image is obtained, to the focal depth of the illumination light. On the other hand, for example, when the information which indicates the definition s is the information which indicates the high-definition mode, the distance interval changing unit 42 changes the distance interval to half of the focal depth of the illumination light. In addition, the distance by which the observation range moves in the z direction may be appropriately changed.

Figure 3A:
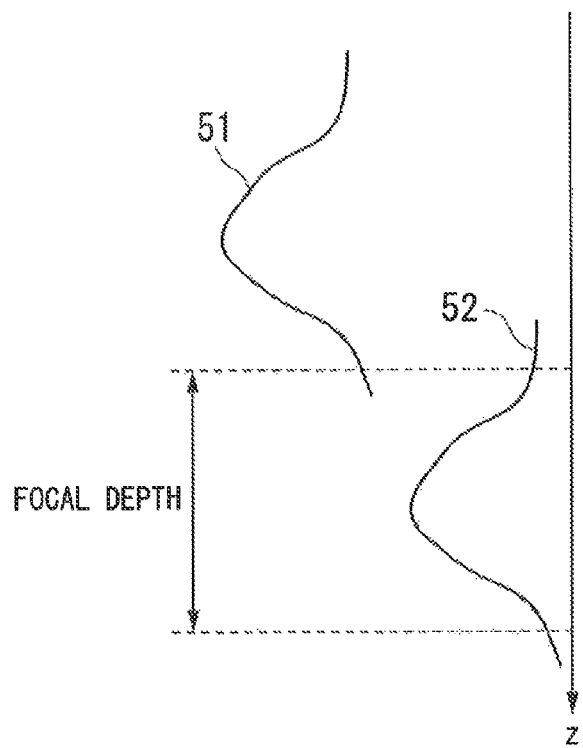
FIG. 3A is a diagram showing a distance in which a stage moves each time the second tomographic image is obtained in a low-definition mode.
Figure 3B:
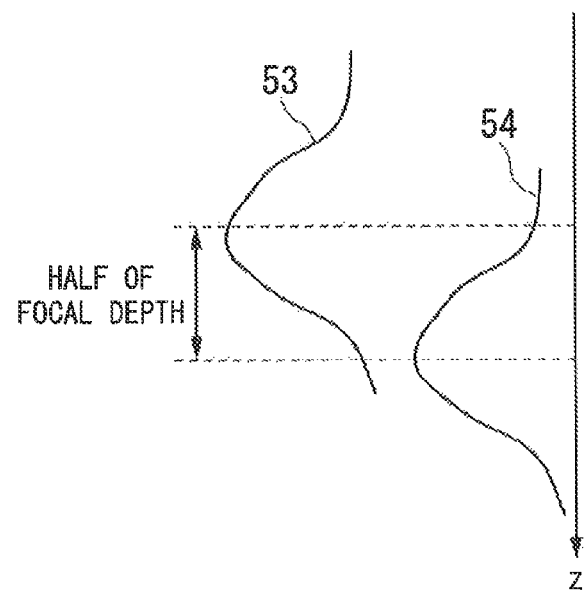
FIG. 3B is a diagram showing a distance in which a stage moves each time the second tomographic image is obtained in a high-definition mode.

The above-described process will be described with reference to FIGS. 3A and 3B. FIGS. 3A and 3B are diagrams showing the distances by which the stage moves each time the second tomographic image is obtained in the low-definition mode and the high-definition mode. In FIG. 3A, in the low-definition mode, intensity distribution 51 of the illumination light which indicates the focal depth in the depth direction (z direction) when a second tomographic image is obtained, and intensity distribution 52 of the illumination light which indicates the focal depth in the depth direction (z direction) after the stage moves to obtain the next second tomographic image are shown. The resolution of the obtained image becomes best at a peak of the intensity distribution 51 (or intensity distribution 52) of the illumination light which indicates the focal depth, and gradually deteriorates as the image becomes distant from the peak.

The range in the z direction, in which the observation can be performed by one-time illumination, is set to the intensity distribution 51 or the intensity distribution 52 which indicates the focal depth. In this case, the stage moves by the focal depth each time the second tomographic image is obtained, and the range, in which the intensity distribution 51 and the intensity distribution 52 which indicate the focal depths in the drawing are overlapped in the z direction, becomes the range in which the second tomographic images are overlapped.

In FIG. 3B, in the high-definition mode, intensity distribution 53 of the illumination light which indicates the focal depth in the depth direction (z direction) when a second tomographic image is obtained, and intensity distribution 54 of the illumination light which indicates the focal depth in the depth direction (z direction) after the stage moves to obtain the next second tomographic image are shown.

In this case, the distance in which the observation ranges are overlapped in the depth direction is half the value of the focal depth. The stage moves by half the value of the focal depth each time the second tomographic image is obtained.

Return to FIG. 1, the distance interval changing unit 42 outputs the changed information, which indicates the distance interval when the optical relative position is changed, to the stage controller 43.

The stage controller 43 supplies control signals, which command moving of the stage by the distance interval supplied from the distance interval changing unit 42, to the stage driving unit 44.

The stage driving unit 44 changes the position of the stage 18 based on the control signals input from the stage controller 43.

Moreover, in the present embodiment, the stage 18 moves with respect to the objective lens unit 16. However, the present invention is not limited to this, and the objective lens unit 16 may move in a state where the relative position relationship of the objective lens unit 16 with respect to the interference optical system 10 is maintained.

That is, an optical relative position changing unit (as an example, the stage driving unit 44) may be any one as long as the relative position of the biological sample which is the observation object and the interference optical system 10 is changed.

The objective lens switching unit 38 outputs switching signals, which indicate the switching of the objective lens, to the revolver driving unit 45, and changes the objective lens, which concentrates the illumination light, from the first objective lens 16_1 to the second objective lens 16_2.

After the objective lens is changed to the second objective lens 16_2, the controller 30 controls so that the image generator 32 obtains the second tomographic image each time the position of the stage 18 is changed by the control of the stage controller 43. That is, the controller 30 controls so that the image generator 32 obtains the second tomographic image each time the optical relative position of the observation object and the interference optical system is changed.

The correlation calculation unit 34 reads the data of the first tomographic image and the data of the second tomographic image from the storage unit 33, and calculates a correlation in the region in which the first tomographic image and the second tomographic image are overlapped each time the relative position of the second tomographic image with respect to the first tomographic image moves.

Specifically, for example, the correlation calculation unit 34 calculates a correlation coefficient R in the region, in which the first tomographic image and the second tomographic image are overlapped, according to the following Equation (1).

[Equation 1]

$$R = \frac{\sum_{k=0}^{N-1}\sum_{j=0}^{M-1}\sum_{i=0}^{L-1}((I(i,j,k)-\bar{I})(T(i,j,k)-\bar{T}))}{\sqrt{\sum_{k=0}^{N-1}\sum_{j=0}^{M-1}\sum_{i=0}^{L-1}(I(i,j,k)-\bar{I})^2 \times \sum_{k=0}^{N-1}\sum_{j=0}^{M-1}\sum_{i=0}^{L-1}(T(i,j,k)-\bar{T})^2}} \quad (1)$$

Here, i, j, and k are the x coordinate, the y coordinate, and the z coordinate in the photographed tomographic image respectively. I (i, j, k) is a luminance value of the second tomographic image (OCT image in which the observation range is narrow) in the overlapped region, and T (i, j, k) is the luminance value of the first tomographic image (OCT image in which the observation range is wide) in the overlapped region. Here, in expression of the following Equation (2), attaching symbol "-" on symbol "I" indicates an abbreviation of I (bar). I (bar) is an average value of the luminance value (i, j, k) of the second tomographic image in the overlapped region, and is expressed by the following Equation (2).

[Equation 2]

$$\bar{I} = \frac{1}{LMN}\sum_{k=0}^{N-1}\sum_{j=0}^{M-1}\sum_{i=0}^{L-1}I(i,j,k) \quad (2)$$

Moreover, similar to I (bar), T (bar) is an abbreviation, and T (bar) is an average value of the luminance value T (i, j, k) of the first tomographic image in the overlapped region and is expressed by the following Equation (3).

[Equation 3]

$$\bar{T} = \frac{1}{LMN}\sum_{k=0}^{N-1}\sum_{j=0}^{M-1}\sum_{i=0}^{L-1}I(i,j,k) \quad (3)$$

The correlation calculation unit 34 outputs information, which indicates the correlation coefficient R in each relative position calculated, to the relative position calculation unit 35. In this case, the correlation between I and T increases as R becomes closer to 1. Accordingly, the correlation calculation unit 34 can determine a position at which the second tomographic image is most similar to the first tomographic image.

Moreover, in the present embodiment, the controller 30 calculates the luminance value and the correlation coefficient R. However, the present invention is not limited to this. That is, the position of the second tomographic image may be determined by calculating other values or the correlation of the shapes of the cells. That is, the position of the second tomographic image may be determined so that a cell object in the first tomographic image and a cell object in the second tomographic image overlap.

Moreover, the controller 30 is not limited to the correlation coefficient R and may perform mapping using a template matching.

The relative position calculation unit 35 determines the relative position of the second tomographic image with respect to the first tomographic image based on the correlation which is calculated by the correlation calculation unit 34. Specifically, for example, the relative position calculation unit 35 derives the position in the relative depth direction and the position in the relative horizontal direction having the highest correlation coefficient R in the range in which x and y are approximately the same as each other, among the correlation coefficients R in each relative position input from the correlation calculation unit 34, and the position in the relative depth direction and the position in the relative horizontal direction which are derived are set to the relative positions of the second tomographic image. The relative position calculation unit 35 outputs the information which indicates the relative position of the second tomographic image, to the pixel value calculation unit 36 along with the information which indicates the luminance value of each second tomographic image.

Moreover, the relative position calculation unit 35 tilts or rotates the pixel positions of respective second tomographic images (high definition images) with environmental factors such as temperature, and thus, may determine the relative position of the second tomographic image with respect to the first tomographic image. This is suitable in a case where the stage is inclined or the stage is rotated when drift is generated.

Moreover, the controller 30 applies auto focus (AF) and detects the drift (temperature drift) of the stage due to the temperature by a sensor, and may determine the relative position of the second tomographic image with respect to the first tomographic image using the value of the temperature drift.

Regarding the image region in which the second tomographic images are overlapped, at each objective position of the region in which two second tomographic images are overlapped, the pixel value calculation unit 36 calculates a shortest position interval between the objective position and each reference point (for example, a center point in the tomographic image) of the tomographic images. In addition, by applying a weighting in which the weight is increased as the shortest position intervals calculated respectively decrease with respect to a measurement value when two second tomographic images are obtained in the objective position, the pixel value calculation unit 36 calculates a combination measurement value at the objective position.

Figure 4:
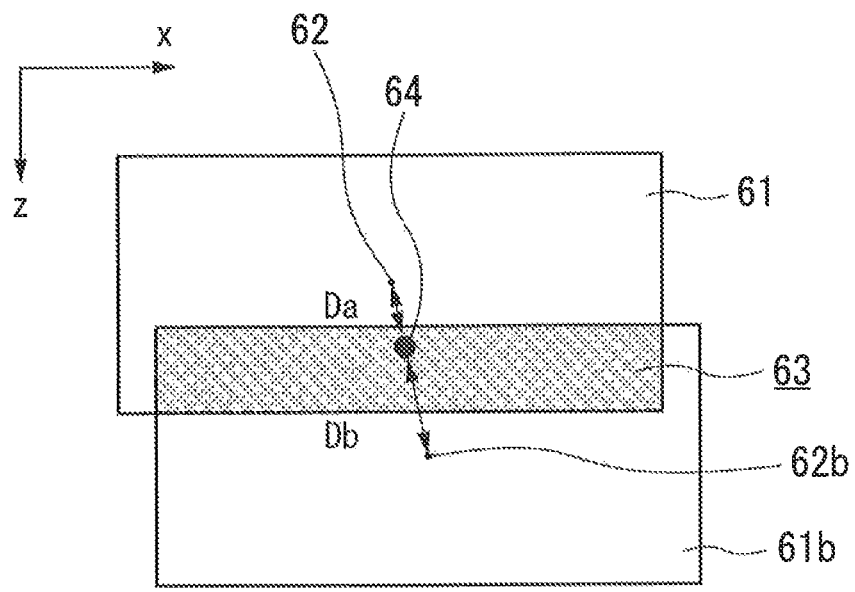
FIG. 4 is a diagram showing an example of one cross-section when two overlapped tomographic images are viewed from the side.

The above-described process will be described with reference to an example of FIG. 4. FIG. 4 is a diagram showing an example of an xz cross-section of two tomographic images which are overlapped. In FIG. 4, one cross-section 61 of the second tomographic image and one cross-section 61b of the second tomographic image are overlapped, and the overlapped region 63 are shown.

Moreover, a first center point 62 in the depth direction (z direction) in the one cross-section 61 of the second tomographic image and a second center point 62b in the depth direction (z direction) in the one cross-section 61b of the second tomographic image are shown.

A position interval from an objective position 64 to the first center point 62 is Da, and a position interval from the objective position 64 to the second center point 62b is Db.

If a luminance value of the objective position 64 in the one cross-section 61 of the second tomographic image is indicated by Ya and a luminance value of the objective position 64 in the one cross-section 61b of the second tomographic image is indicated by Yb, for example, the pixel value calculation unit 36 calculates a luminance value Y of the objective position as the combination measurement value according to the following Equation (4).

$$Y=(Ya\times Db+Yb\times Da)/(Da+Db) \quad (4)$$

The pixel value calculation unit 36 outputs the calculated information, which indicates the combination measurement value of each objective position positioned in the region where the second tomographic images are overlapped with each other, to the combining unit 46.

The combining unit 46 combines the first tomographic image and a second combination image based on the relative position which is detected by the detector 40. More specifically, the combining unit 46 combines the first tomographic image and the second tomographic image based on the relative position detected by the detector 40 and the combination measurement value which is calculated by the pixel value calculation unit 36.

Specifically, for example, the combining unit 46 directly sets each pixel value as the pixel value of the position, in the image region in which the second tomographic images are not overlapped. On the other hand, the combining unit 46 sets the combination measurement value supplied from the pixel value calculation unit 36 as the pixel value of the position, in the image region in which the second tomographic images are overlapped. Accordingly, the combining unit 46 generates the combination tomographic image which combines the first tomographic image and the second tomographic image. The combining unit 46 stores the generated combination tomographic image in the storage unit 33. Moreover, the controller 30 displays the data of the combination tomographic image which is combined by the combining unit 46 on the display unit 47. This is an example which reflects the measurement value closer to the center of the focus spot to the tomographic image.

Figure 5:
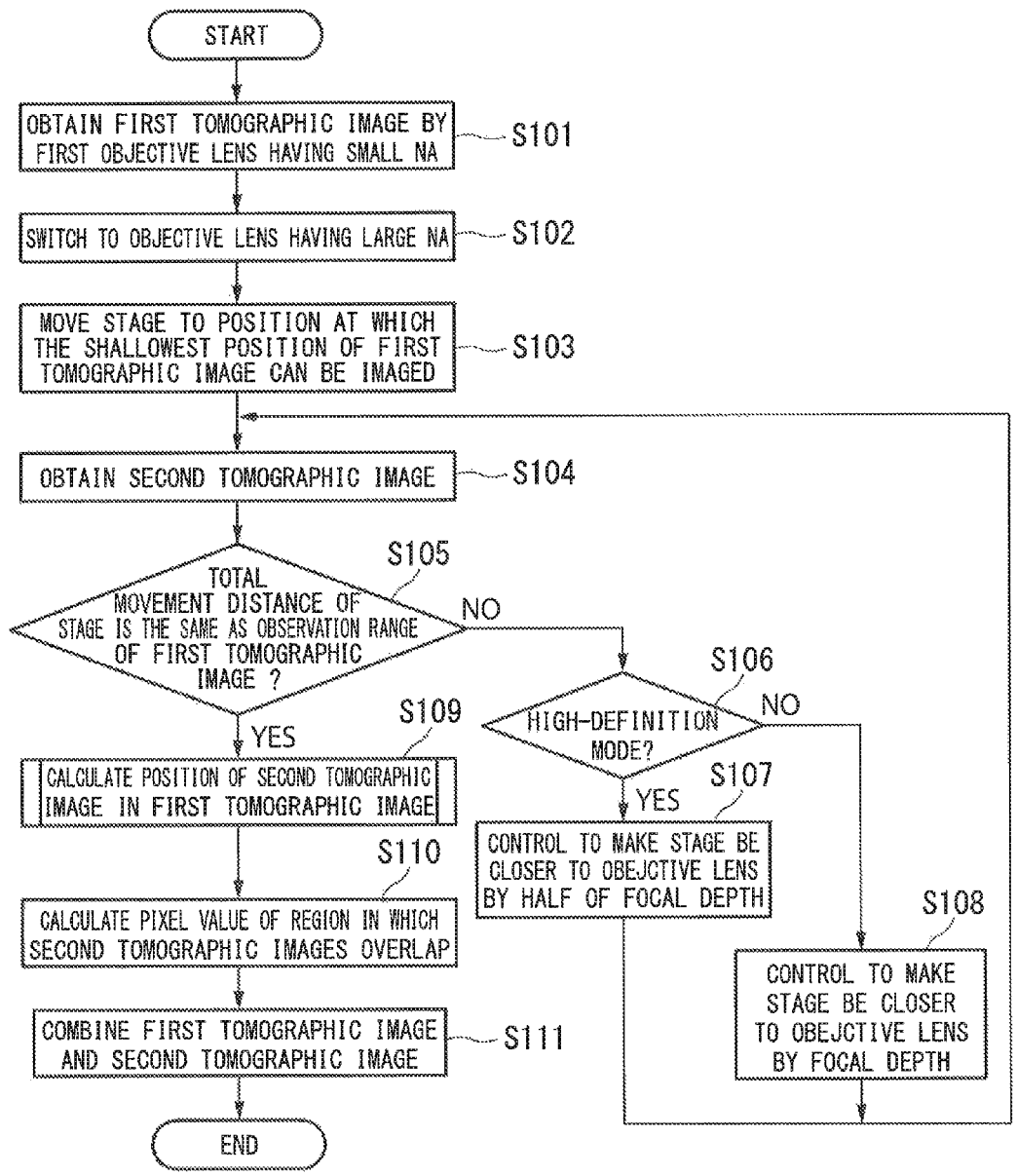
FIG. 5 is a flowchart showing a flow of process of the optical coherence tomography observation apparatus according to the first embodiment.

FIG. 5 is a flowchart showing a flow of the process of the optical coherence tomography observation apparatus 1 according to the first embodiment. First, the controller 30 controls to obtain the first tomographic image by the first objective lens 16_1 having a small NA (Step S101). Subsequently, the objective lens switching unit 38 of the controller 30 controls to switch to the second objective lens 16_2 having a large NA (Step S102).

Subsequently, the stage controller 43 of the controller 30 controls to move the stage to a position at which the shallowest position (may be an appropriate position) of the first tomographic image can be imaged (Step S103). Subsequently, the controller 30 controls to obtain the second tomographic image (Step S104).

Subsequently, it is determined whether or not the total movement distance of the stage is the same as the observation range of the first tomographic image (Step S105). That is, it is determined whether or not the second tomographic image has obtained all images in the z direction of the first tomographic image.

When the tomographic image is not obtained in all depths included in the first tomographic image (NO in Step S105), the controller 30 determines whether or not it is a high-definition mode (Step S106). When it is the high-definition mode (YES in Step S106), the stage controller 43 controls so as to put the stage closer to the second objective lens 16_2 just as half of the focal depth (Step S107), and obtains the next second tomographic image (return to the process of Step S104). On the other hand, when it is not the high-definition mode (NO in Step S106), the stage controller 43 controls so as to put the stage closer to the second objective lens 16_2 just as the focal depth (Step S108), and returns to the process of Step S104.

In Step S105, when the tomographic image is obtained in all depths included in the first tomographic image (YES in Step S105), the relative position calculation unit 35 calculates the position of the second tomographic image with respect to the first tomographic image in the flow of the process shown in FIG. 6 described below (Step S109). Subsequently, the pixel value calculation unit 36 calculates the pixel value of the region in which the second tomographic images are overlapped (Step S110). Subsequently, the combining unit 46 combines the first tomographic image and the second tomographic image (Step S111). As described above, the processes of the flowchart end.

Figure 6:
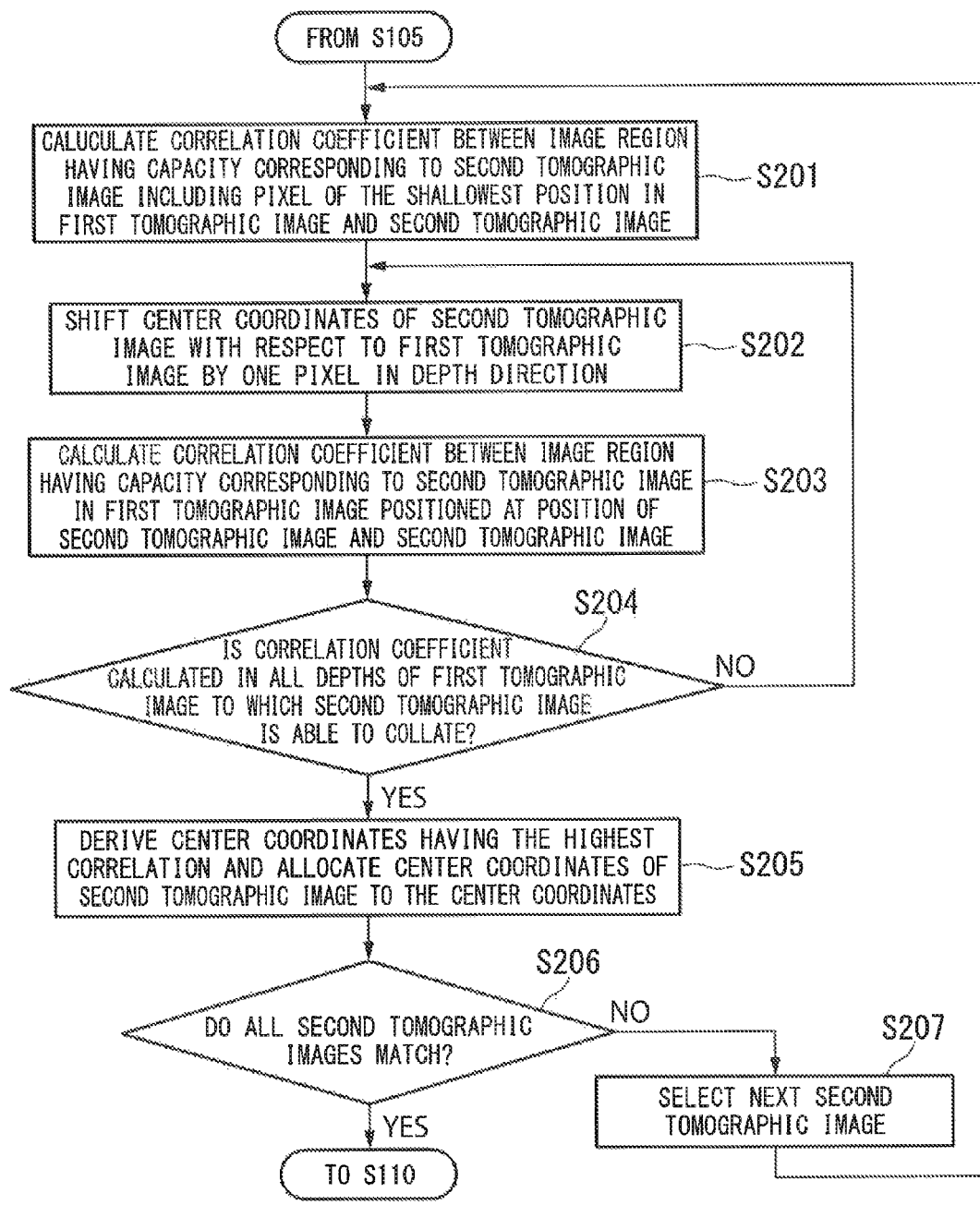
FIG. 6 is a flowchart showing the flow of the process of a controller in Step S109 of FIG. 5.

FIG. 6 is a flowchart showing the flow of the process of the controller 30 in Step S109 of FIG. 5. First, the correlation calculation unit 34 calculates the correlation coefficient R between the image region having capacity corresponding to the second tomographic image including the pixel of the shallowest position in the first tomographic image, and the second tomographic image (Step S201). Subsequently, the correlation calculation unit 34 shifts the center coordinates of the second tomographic image with respect to the first tomographic image by one pixel in the depth direction (Step S202).

Subsequently, the correlation calculation unit 34 calculates the correlation coefficient R between the image region having capacity corresponding to the second tomographic image in the first tomographic image corresponding to the position of the second tomographic image, and the second tomographic image (Step S203). Subsequently, the correlation calculation unit 34 determines whether or not the correlation coefficient R is calculated in all depths of the first tomographic image to which the second tomographic image is able to collate (Step S204).

When the correlation coefficient R is not calculated in all depths of the first tomographic image to which the second tomographic image is able to collate (NO in Step S204), the correlation calculation unit 34 is returned to the process of Step S202. On the other hand, when the correlation coefficient R is calculated in all depths of the first tomographic image to which the second tomographic image is able to collate (YES in Step S204), the relative position calculation unit 35 derives center coordinates having the highest correlation, and, as the position of the second tomographic image in the first tomographic image, sets the center coordinates of the second tomographic image as the derived center coordinates (Step S205).

Subsequently, the relative position calculation unit 35 determines whether or not all second tomographic images are determined to be allocated to any position in the first tomographic image (Step S206). When it is not determined that all second tomographic images are allocated to any position in the first tomographic image (NO in Step S206), the controller 30 selects the next second tomographic image (Step S207) and is returned to the process of Step S201. On the other hand, when it is determined that all second tomographic images are allocated to any position in the first tomographic image (YES in Step S206), the process of the relative position calculation unit 35 ends. As described above, the processes of the flowchart end.

As mentioned-above, the controller 30 obtains the first tomographic image using the first objective lens 16_1.

Moreover, the controller 30 obtains the second tomographic image so that the second tomographic images are partially overlapped with each other, using the second objective lens 16_2 having the higher NA than the first objective lens 16_1. Moreover, after the second tomographic image is obtained, the controller 30 calculates the correlation coefficient R between the second tomographic image and the first tomographic image, and determines to which position the second tomographic image is allocated in the first tomographic image based on the correlation coefficient R.

Accordingly, even when the stage or the optical system is not able to correctly moved, the controller 30 connects the second tomographic images having high lateral resolution and a narrow observation range in the depth direction, and thus, the tomographic image having a wide observation range in the depth direction and high definition can be obtained.

In addition, since the image having high lateral resolution is obtained as the image is close to the focal position of the illumination light, in the high-definition mode, by obtaining a wide region in which the second tomographic images are overlapped, the controller 30 is able to obtain a tomographic image having more higher definition.

Moreover, in the present embodiment, the controller 30 sets the movement distance of the stage 18 each time the second tomographic image is obtained to the focal depth or less of the second objective lens 16_2, and generates the overlapping of the second tomographic images. However, the present invention is not limited to this, and the movement distance of the stage 18 may be set to a distance corresponding to the focal depth. In this case, in a position which is deviated from the focal position, even when the image is positioned in the focal depth, the image quality (sharpness and the like) becomes slightly worse than the focal position. However, since the obtained sheets of the second tomographic images can be decreased, the measurement time can be shortened.

Second Embodiment

Subsequently, a second embodiment will be described. In the optical coherence tomography observation apparatus 1 of the first embodiment, the first tomographic image having the wide observation range is obtained by the first objective lens having the low NA, and the second tomographic image having the narrow observation range is obtained by the second objective lens having the high NA. Moreover, the optical coherence tomography observation apparatus 1 determines to which position in the first tomographic image the second tomographic image is allocated, and connects the second tomographic image, and thus, the tomographic image having the wide observation range in the depth direction and high definition is obtained.

An optical coherence tomography observation apparatus 1b in the second embodiment includes a diaphragm unit 14 (light control unit, switching unit, and selection unit) which reduces the illumination light, and the diaphragm unit 14 further reduces a light flux diameter of the illumination light when the first tomographic image is obtained compared with the light flux diameter of the illumination light when the second tomographic image is obtained. In this way, it is preferable that the light flux of the first illumination light be more reduced than the light flux of the second illumination light.

Accordingly, even when the optical coherence tomography observation apparatus 1b does not change the objective lens, the second tomographic image having higher lateral resolution and a narrower observation range in the depth direction than the first tomographic image can be obtained by opening the diaphragm, and thus, the tomographic image having a wide observation range in the depth direction and high definition can be obtained by connecting the second tomographic image.

Figure 7:
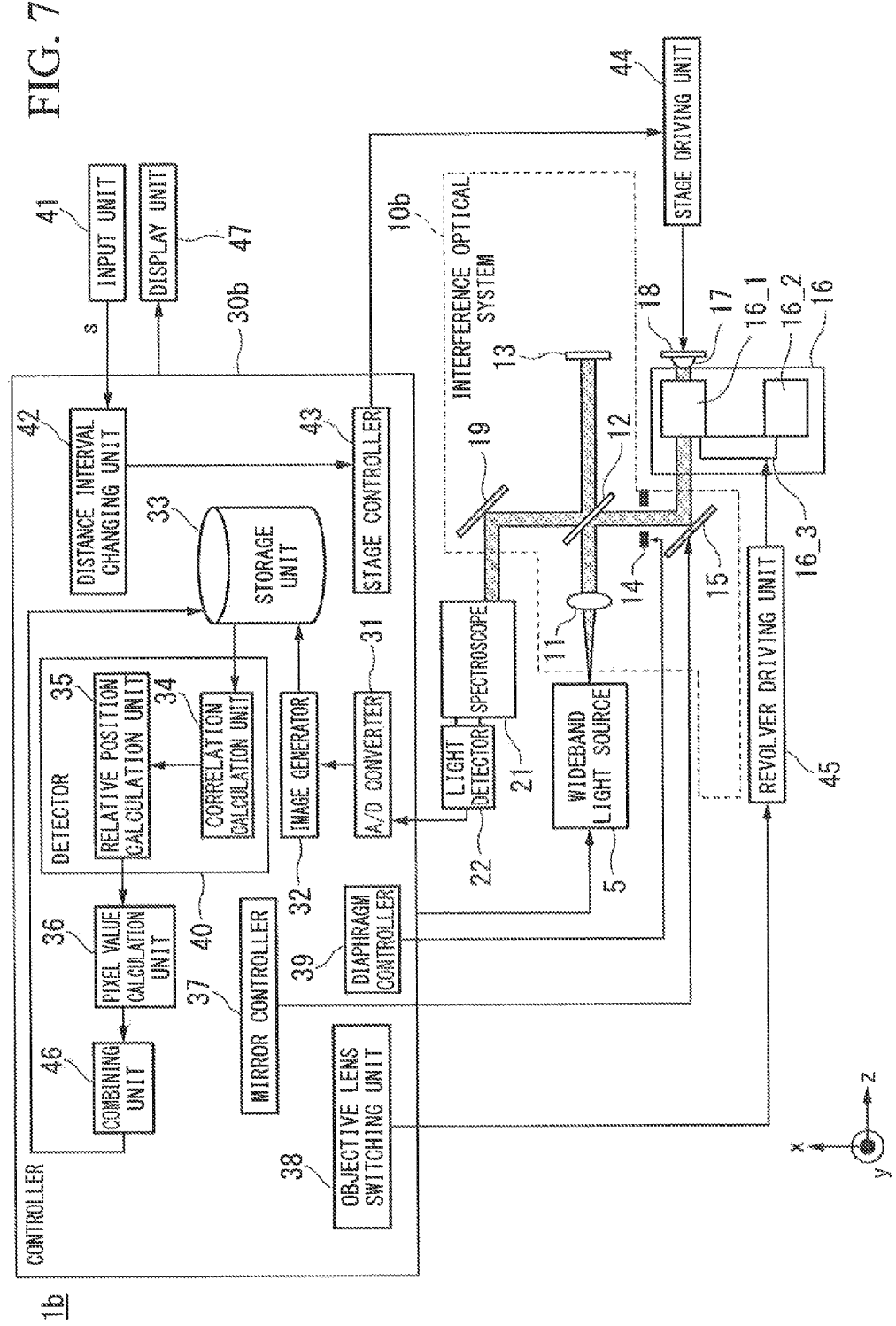
FIG. 7 is a block configuration diagram of an optical coherence tomography observation apparatus according to a second embodiment.

FIG. 7 is a block configuration diagram of the optical coherence tomography observation apparatus 1b according to the second embodiment. In addition, the same reference numerals are attached to the elements common to those of FIG. 1, and detailed descriptions thereof are omitted here.

With respect to the configuration of the optical coherence tomography observation apparatus 1 of FIG. 1, in the configuration of the optical coherence tomography observation apparatus 1b of FIG. 7, the interference optical system 10 is changed to an interference optical system 10b, a diaphragm unit 14 is added to the interference optical system 10b, the controller 30 is changed to a controller 30b, and a diaphragm controller 39 (light control unit, switching unit, and selection unit) is added to the controller 30b.

The diaphragm unit 14 is positioned between the beam splitter 12 and the galvanomirror 15. The diaphragm unit 14 reduces the illumination light guided from the beam splitter 12 by the control of the diaphragm controller 39, and guides the reduced illumination light to the galvanomirror 15. The galvanomirror 15 guides the reduced illumination light to the first objective lens 16_1, and the first objective lens 16_1 concentrates the reduced illumination light to the biological sample which is the observation object.

It is preferable that the position of the diaphragm unit 14 be close to the exit pupil position of the objective lens, that is, the position of the galvanomirror 15. Moreover, in the present embodiment, the diaphragm unit 14 is positioned between the beam splitter 12 and the galvanomirror 15. However, the present invention is not limited to this, and the diaphragm unit 14 may be positioned between the galvanomirror 15 and the biological sample 17 which is the observation object.

When the first tomographic image having the narrow observation range in the depth direction is obtained, the controller 30b controls the diaphragm controller 39 so as to make the diaphragm at a predetermined opening. In addition, when the second tomographic image having the wide observation range in the depth direction is obtained, the controller 30b controls the diaphragm controller 39 so that the diaphragm is opened more than when the first tomographic image is obtained.

Figure 8:
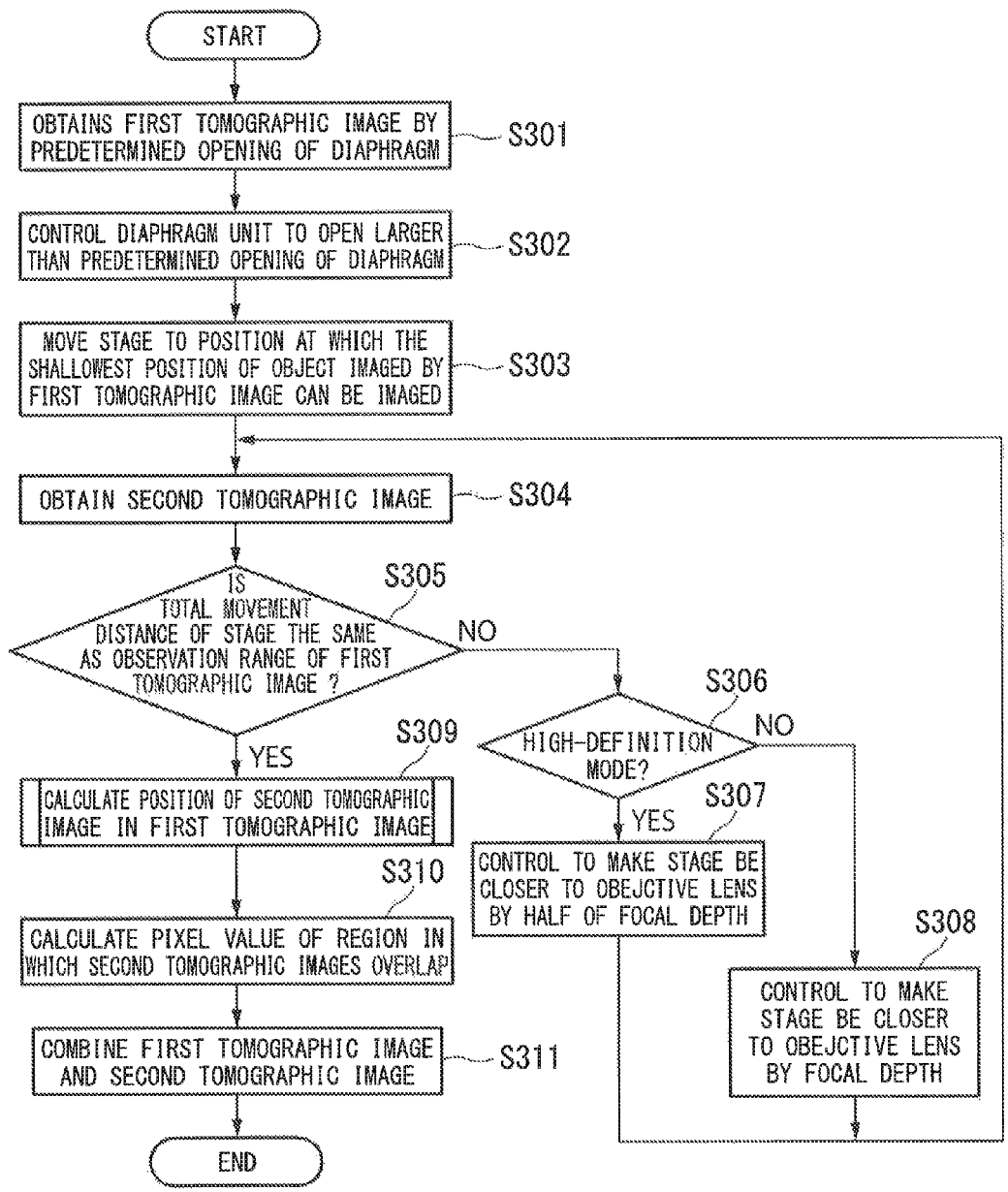
FIG. 8 is a flowchart showing a flow of process of the optical coherence tomography observation apparatus according to the second embodiment.

FIG. 8 is a flowchart showing a flow of the process of the optical coherence tomography observation apparatus 1b according to the second embodiment. First, the controller 30b obtains the first tomographic image with a predetermined opening of the diaphragm (Step S301). The diaphragm controller 39b controls the diaphragm unit 14 so that the diaphragm is opened more than a predetermined opening of diaphragm in which the first tomographic image was obtained (Step S302).

The processes from Step S303 to Step S311 are the same as Step S103 to Step S111 in FIG. 5, and thus, descriptions thereof are omitted here. As described above, the process of the flowchart ends.

In the optical coherence tomography observation apparatus 1b of the second embodiment, even when the objective lens is not changed, the second tomographic image having higher lateral resolution and a narrower observation range in the depth direction than the first tomographic image can be obtained by further opening the diaphragm than when the first tomographic image is obtained, and thus, the tomographic image having high definition can be obtained by connecting the second tomographic image.

Moreover, in all embodiments, the controllers (30 and 30b) obtain the first tomographic image at a predetermined frame interval, and when the change of the luminance distribution between the frames exceeds a predetermined range, the controller may be controlled to obtain the second tomographic image.

In addition, in all embodiments, the controllers (30 and 30b) obtain the first tomographic image at a predetermined frame interval, and when the change of the luminance distribution between the frames exceeds a predetermined range, the controller may be controlled to obtain the second tomographic image with respect to the image region in which the change of the luminance distribution exceeds the predetermined range.

Figure 9:
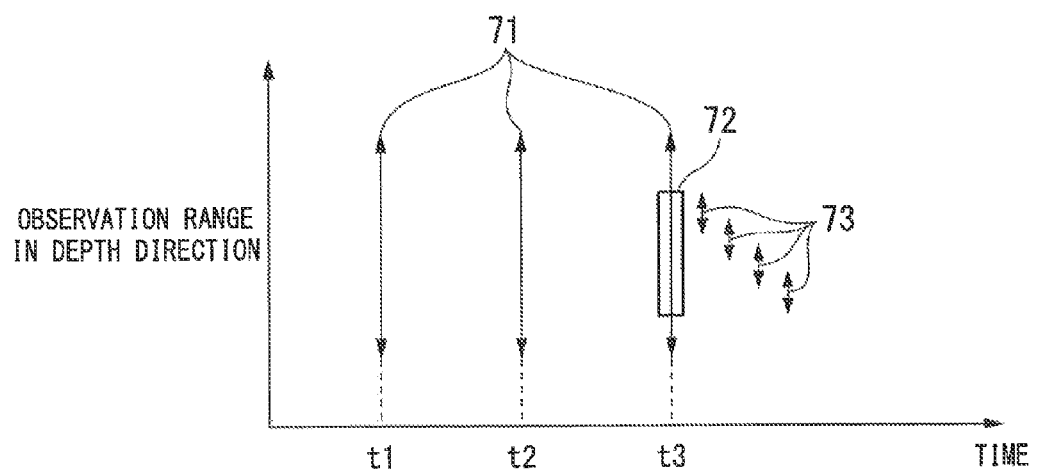
FIG. 9 is a diagram showing an example in which the second tomographic image is obtained with respect to an image region in which a change of luminance distribution exceeds a predetermined threshold value.

The process will be described with reference to FIG. 9. FIG. 9 is a diagram showing an example in which the first tomographic image is obtained at a predetermined frame interval, and when the change of the luminance distribution between the frames exceeds a predetermined threshold value, the second tomographic image is obtained with respect to the image region in which the change of the luminance distribution exceeds the predetermined threshold value. In FIG. 9, a vertical axis indicates the observation range in the depth direction, and a horizontal axis indicates time. In FIG. 9, an observation range 71 of the first tomographic image, a range 72 in which the change of the luminance distribution between the frames exceeds a predetermined range, and four observation ranges 73 of the second tomographic image are shown.

The controllers (30 and 30b) compare the luminance value of the tomographic image at a current time and the luminance value of the tomographic image at the time immediately before the current time, and determine whether or not the change of the luminance distribution between frames exceeds a predetermined range.

For example, in FIG. 9, since the change of the luminance distribution between frames does not exceed a predetermined range at time t1 and time t2, the controllers (30 and 30b) obtain only the first tomographic image having a narrow observation range in the depth direction.

On the other hand, at time t3, for example, since the change of the luminance distribution between frames exceeds a predetermined range, the controllers (30 and 30b) are controlled to obtain four second tomographic images each time the stage 18 moves in the range 72 in which the change of the luminance distribution exceeds a predetermined range.

Moreover, in all embodiments, the optical coherence tomography observation apparatuses (1 and 1b) are described using the optical coherence tomography observation apparatus of the Fourier domain method. However, the present invention is not limited to this, and the same method can be also applied to the optical coherence tomography observation apparatus of a time domain method.

In addition, in all embodiments, in the optical coherence tomography observation apparatuses (1 and 1b), when a plurality of locations having the highest correlation coefficient R exist, by narrowing a matching range in the first tomographic image (OCT image) for reference to a predetermined range in the first tomographic images, a matching position may be derived.

In all embodiments, the biological sample is used as the object to be photographed. However, the present invention is not limited to this, and the object to be photographed may be any one as long as the observation object is a transparent scatterer.

Moreover, in all embodiments, the controllers (30 and 30b) move the galvanomirror 15, the second tomographic image is obtained in a depth of the observation object, and thereafter, obtaining the second tomographic image each time the stage 18 moves in the depth direction is repeated. However, the present invention is not limited to this.

Moreover, in all embodiments, the controllers (30 and 30b) do not move the galvanomirror 15, the second tomographic image is obtained at a point in two dimensions, and thereafter, obtaining the second tomographic image each time the stage 18 moves in the depth direction is repeated, and a plurality of sheets of the second tomographic image may be obtained the point in two dimensions. In this case, after all second tomographic images are obtained the point in two dimensions, the controllers (30 and 30b) move the galvanomirror 15, and the tomographic images for other points in two dimensions may be similarly obtained.

Moreover, in all embodiments, by obtaining the correlation between the first tomographic image and the second tomographic image each time the second tomographic image is obtained, and thereby the relative position may be determined.

Moreover, in the optical coherence tomography observation apparatuses (1 and 1b) of the embodiments of the present invention, by obtaining two sheets of the first tomographic image at a predetermined time interval using the first objective lens, deriving an unchanged still region by two tomographic images based on the obtained two sheets of the tomographic images, and thereby the correlation may be obtained in only the derived still region. Accordingly, in the controllers (30 and 30b), the calculation processing amount can be decreased, and the time used to obtain a high-definition tomographic image, which is made by connecting the second tomographic image, can be shortened.

Moreover, in the optical coherence tomography observation apparatuses (1 and 1b) of the embodiments of the present invention, by obtaining dyed images of the cells which are dyed by fluorochromes using the first objective lens, deriving the image regions of the cells dyed by the fluorochromes from the dyed images, and thereby the second tomographic images may be obtained using the second objective lens (the objective lens having a high NA) with respect to only the image regions of the derived cells. Accordingly, in the controllers (30 and 30b), the calculation processing amount can be decreased, and the time used to obtain a high-definition tomographic image, which is made by connecting the second tomographic image, can be shortened.

Moreover, in all embodiments, in all image regions in the first tomographic image, the correlation calculation unit 34 calculates correlation coefficient R between the image region having the capacity corresponding to the second tomographic image in the image region of the first tomographic image, and the second tomographic image. However, the present invention is not limited to this.

The correlation calculation unit 34 may derive a first representative region from the first tomographic image, and may obtain a correlation between the luminance value of the pixel of the first representative region and the luminance value of the second tomographic image.

Accordingly, in the correlation calculation unit 34, since the frequency of obtaining the correlation can be decreased, the calculation processing amount is decreased, and the time used to obtain the high-definition tomographic image, which is made by connecting the second tomographic image, can be shortened.

Moreover, the controllers (30 and 30b) derive a characteristic region relating to the luminance distribution of the first tomographic image from the first tomographic image, and may be controlled to obtain the second tomographic image with respect to only the derived characteristic region.

Specifically, for example, the controllers (30 and 30b) may calculate the luminance change for each predetermined pixel interval from the first tomographic image, may derive the image region in which the calculated luminance change exceeds a predetermined threshold value, and may be controlled to obtain the second tomographic image with respect to the derived image region.

Moreover, since the first tomographic image is generated at a predetermined time interval, the controllers (30 and 30b) may derive a specific region in which the measurement values are approximately constant from a plurality of first tomographic images, and may set only the specific region as the object, in which the correlation is to be calculated, to the detector 40.

Moreover, the controllers (30 and 30b) may derive an image region in which the luminance value of the first tomographic image exceeds a predetermined threshold value, and may control to obtain the second tomographic image with respect to the derived image region.

In addition, the controllers (30 and 30b) may derive edges from the first tomographic image, and may be controlled to obtain the second tomographic image with respect to the image region which is surrounded by the derived edges.

Accordingly, since the controllers (30 and 30b) derive the characteristic region relating to the luminance distribution of the first tomographic image and obtain the second tomographic image with respect to only the derived characteristic region, the second tomographic image having high definition can be obtained with respect to only the image region in which an object (for example, cell) to be imaged exists. In addition, in the controllers (30 and 30b), the calculation processing amount can be decreased, and the time used to obtain the high-definition tomographic image, which is made by connecting the second tomographic image, can be shortened.

In addition, the controllers (30 and 30b) may be controlled to obtain the first tomographic image at a predetermined time interval (frame interval) and to obtain the second tomographic image at a predetermined time.

Accordingly, when it is understood in advance that a change is generated at a predetermined time, the controllers (30 and 30b) obtain the second tomographic image having high resolution at only the predetermined time, and thus, the calculation processing amount can be decreased compared to the case where the second tomographic image is obtained through measurement time.

Moreover, at the time when high resolution is not needed, the controllers (30 and 30b) do not obtain the second tomographic image, and thus, the amount of the second tomographic image data stored in the storage unit 33 can be decreased compared to the case where the second tomographic image is obtained through measurement time.

Moreover, a case where the flux of the second illumination light from which the second tomographic image is obtained is the same as the flux of the first illumination light from which the first tomographic image is obtained is assumed. That is, the observation ranges in the depth directions of the first tomographic image and the second tomographic image are the same as each other. Here, the second illumination light is a light flux which is illuminated to approximately the same region (is illuminated to substantially the same region even though the light flux cannot be illuminated to completely the same region due to the temperature drift or the like) as the first illumination light.

In this case, the distance interval changing unit 42 changes the distance interval when the optical relative position is changed so that the first tomographic image and the second tomographic image are overlapped. Moreover, in the controllers (30 and 30b), the correlation calculation unit 34 of the controllers (30 and 30b) obtains the correlation in the region in which the first tomographic image and the second tomographic image are overlapped, and the controllers (30 and 30b) may connect the first tomographic image and the second tomographic image to each other based on the correlation.

Moreover, in all embodiments, the beam splitter 12 is described as an example in which the light division unit and the light combining unit are integrally configured. However, the present invention is not limited to this. For example, the light division unit and the light combining unit may be separately configured using a polarizer.

Moreover, in all embodiments, the reflective type optical coherence tomography observation apparatus is described.

However, the present invention may be also applied to a transmissive type optical coherence tomography observation apparatus.

<Modification>

In all embodiments, the light control unit of the optical coherence tomography observation apparatuses (1 and 1*b*) forms the illumination light having a plurality of numerical apertures. However, the present invention is not limited to this. As a modification, the light control unit may form interference light having the plurality of numerical apertures. In this case, in the interference optical systems (10 and 10*b*) of the optical coherence tomography observation apparatuses (1 and 1*b*), a condensing lens is provided between the beam splitter 12 and the light detector 22, and a small aperture portion is provided between the condensing lens and the light detector 22.

The condensing lens (light control unit, switching unit, and selection unit) concentrates the interference light, which is combined by the beam splitter 12, to the light detector 22.

The small aperture portion (light control unit, switching unit, and selection unit) includes an aperture having a variable diameter at a position conjugate to the focus spot of the first objective lens or the second objective lens. The small aperture portion guides only light of the aperture size in the interference light concentrated by the condensing lens into the light detector 22.

Accordingly, the interference optical systems (10 and 10*b*), in which the condensing lens and the small aperture portion are further installed, become close to Optical Coherence Microscopy (OCM) which also uses a confocal effect.

The optical coherence tomography observation apparatuses (1 and 1*b*) according to the above-described embodiments correspond to a state where NA of the condensing lens is decreased and the small aperture portion is increased (in this state, the observation range in the z direction is wide and the lateral resolution is low).

On the other hand, in the optical coherence tomography observation apparatus according to the modification, the interference optical systems (10 and 10*b*) have a function as an illumination optical system which illuminates the observation object by illumination light and a function as an observation optical system which observes the light from the observation object which is obtained by illuminating the illumination light and forms an image. In the illumination optical system, the observation range in the z direction is wide and the lateral resolution is low.

As the function as the light control unit, the controllers (30 and 30*b*) switch the observation optical system by controlling the size of the aperture of the small aperture portion. Specifically, the light control unit decreases the size of the aperture of the small aperture portion to be smaller than a predetermined size, and the observation optical systems having the wide observation range in the z direction and the low lateral resolution is switched to the observation optical system having the narrow observation range in the z direction and the high lateral resolution.

Accordingly, in the optical coherence tomography observation apparatus according to the modification, the first tomographic image having the wide observation range in the z direction and the low lateral resolution and the second tomographic image having the narrow observation range in the z direction and the high lateral resolution can be obtained.

Moreover, in general OCM, the aperture of the illumination system and the aperture of the detection system are not separate but common, and the modification can also be applied to the system of the general OCM.

Moreover, in the optical coherence tomography observation apparatus of the modification, when the illumination optical system and the observation optical system are configured by the common optical system, the condensing lens is not provided, and the light control unit changes the numerical apertures of the illumination light and the interference light.

Specifically, the objective lens switching unit 38 of the controller 30 switches the first objective lens 16_1 and the second objective lens 16_2, or the diaphragm controller 39 of the controller 30*b* changes the numerical aperture of the illumination light and the numerical aperture of the interference light by switching the diaphragm. Here, the numerical aperture indicates an angle which is formed between the focus spot of the optical system and an effective aperture of the light flux formed by the optical system.

When the tomographic image having a wide observation range in the z direction and low lateral resolution is obtained, the controllers (30 and 30*b*) decrease the numerical aperture of the illumination light and increase the aperture of the small aperture portion.

On the other hand, when the tomographic image having a narrow observation range in the z direction and high lateral resolution is obtained, the controllers (30 and 30*b*) increase the numerical aperture of the illumination light and decrease the aperture of the small aperture portion.

Moreover, in the optical coherence tomography observation apparatus of the modification, when the illumination optical system and the observation optical system are configured of independent optical systems, the optical coherence tomography observation apparatus of the modification includes a first condensing lens which concentrates the interference light to the light detector 22 and a second condensing lens which has a larger numerical aperture than that of the first condensing lens and concentrates the interference light to the light detector 22. In addition, the light control unit decreases NA of the objective lens of the illumination system and changes the numerical aperture of the illumination light.

When the tomographic image having a wide observation range in the z direction and low lateral resolution is obtained, the controllers (30 and 30*b*) decrease the numerical aperture of the interference light and increase the aperture of the small aperture portion in the observation optical system by switching the first condensing lens and the second condensing lens having a larger numerical aperture than that of the first condensing lens.

On the other hand, when the tomographic image having a narrow observation range in the z direction and high lateral resolution is obtained, the controllers (30 and 30*b*) increase the numerical aperture of the interference light in the observation optical system and decrease the aperture of the small aperture portion by switching the first condensing lens and the second condensing lens.

However, in the optical coherence tomography observation apparatus of the modification, when the tomographic image having a wide observation range in the z direction and low lateral resolution is obtained, it is preferable that the numerical aperture of the spectroscope be satisfied in a state where the numerical aperture of the illumination light in the illumination optical system or the numerical aperture of the interference light in the observation optical system is decreased.

If the above-described matters are summarized, it can be said that at least one of the illumination optical system and the observation optical system includes the diaphragm device for reducing the light flux diameter of the illumination light or the light from the observation object.

Moreover, by recording programs which perform each process of the controllers (30 and 30*b*) of the present embodiment on a computer readable recording medium, and reading the programs, which are recorded on the recording medium, by using a computer system and executing the programs, the above-described various processes related to the controllers (30 and 30b) may be performed.

Moreover, here, the "computer system" may include OS or hardware such as peripheral equipment. In addition, the "computer system" also includes homepage provision environment (or display environment) as long as WWW system is used. Moreover, the "computer readable recording medium" means writable nonvolatile memory such as a flexible disk, a magneto-optical disk, ROM, or flash memory, a portable medium such as a CD-ROM, and a storage device such as a hard disk which is built in the computer system.

Furthermore, the "computer readable recording medium" includes a medium which holds programs during some period of time such as volatile memory (for example, a Dynamic Random Access Memory (DRAM)) inside a computer system which becomes a server or a client when programs are transmitted via a network such as the internet or a communication circuit such as a telephone line. Moreover, the programs may be transmitted to other computer systems via a transmission medium or transmission waves in the transmission medium from the computer system which stores the programs in a storage device or the like. Here, the "transmission medium" which transmits the programs means a medium such as a network (communication network) such as the internet or a communication circuit (communication line) such as a telephone line, which have a function which transmits information. Moreover, the programs may be a program for achieving a portion of the above-described functions. Furthermore, the programs may be a program which can be achieved by combination with the programs in which the above-described functions are recorded on the computer system in advance, that is, a so-called difference file (difference program).

As described above, embodiments of the present invention are described in detail with reference to the drawings. However, the specific configuration is not limited to the embodiments, and also includes a design within the scope which does not depart from the gist of the present invention, or the like.

DESCRIPTION OF THE REFERENCE SYMBOLS

1 and 1b: optical coherence tomography observation apparatus
5: wideband light source (light source)
10 and 10b: interference optical system
12: beam splitter
13: reference mirror
15: galvanomirror
16_1: first objective lens
16_2: second objective lens
21: spectroscope
22: light detector (light detection unit)
30 and 30b: controller
32: image generator
33: storage unit
34: correlation calculation unit
35: relative position calculation unit
36: pixel value calculation unit
39: diaphragm controller
40: detector
42: distance interval changing unit
46: combining unit

What is claimed is:

1. An optical coherence tomography observation apparatus, comprising:
    an interference optical system that has a splitting device that is configured to split incident light into reference light and illumination light, and an optical combining device that is configured to make the reference light and a measurement light interfere with each other, the measurement light being obtained from an observation object which is illuminated with the illumination light, the interference optical system having function as an illumination optical system and as an observation optical system, the illumination optical system being configured to illuminate the observation object with the illumination light, the observation optical system being configured to observe the measurement light;
    a light detection unit that is configured to detect interference light obtained from the interference by the optical combining device;
    a light control unit that is configured to change a plurality of numerical apertures, at least one optical system of the illumination optical system and the observation optical system having the light control unit;
    an image generator that is configured to generate a first tomographic image which is within a first observation range of the observation object based on first interference light and to generate second tomographic images which are within a second observation range of the observation object based on second interference light, the first interference light being detected by the light detection unit in a state where the light control unit is set to a first numerical aperture, the second interference light being detected by the light detection unit in a state where the light control unit is set to a second numerical aperture which is larger than the first numerical aperture, the second observation range being smaller than the first observation range, a position of the second tomographic image in the observation object is moved in a depth direction of the observation object; and
    a detector that is configured to detect a relative position for each of the second tomographic image generated by the image generator with respect to the first tomographic image generated by the image generator, at which a correlation of the second tomographic image with the first tomographic image becomes highest.

2. The optical coherence tomography observation apparatus according to claim 1, further comprising:
    a diaphragm as the light control unit.

3. The optical coherence tomography observation apparatus according to claim 1, further comprising:
    a first objective lens that is configured to concentrate the illumination light to the observation object, and
    a second objective lens that is configured to have a larger numerical aperture than a numerical aperture of the first objective lens and concentrate the illumination light to the observation object,
    wherein the light control unit switches the first objective lens and the second objective lens.

4. The optical coherence tomography observation apparatus according to claim 1, further comprising:
    a combining unit that is configured to combine the first tomographic image and the second tomographic image based on a relative position detected by the detector.

5. The optical coherence tomography observation apparatus according to claim 4,
    wherein a plurality of second tomographic images are generated in a depth direction, wherein the optical coherence tomography observation apparatus further comprises a pixel value calculation unit that is configured to calculate a combination measurement value at an objective position by applying a weighting with respect to a measurement value when two second tomographic images are obtained in the objective position based on an interval between the objective position and a reference point in each tomographic image at each objective position located at a region in which two second tomographic images overlap, and wherein the combining unit is configured to combine the first tomographic image and the second tomographic image based on the relative position which is detected by the detector and the combination measurement value calculated by the pixel value calculation unit.

6. The optical coherence tomography observation apparatus according to claim 1, wherein the detector is configured to derive a first representative region from the first tomographic image, and obtain a correlation between a measurement value of the first representative region and a measurement value of the second tomographic image.

7. The optical coherence tomography observation apparatus according to claim 1, wherein the image generator is configured to generate the second tomographic image at a characteristic region which relates to a distribution of a measurement value of the first tomographic image, the characteristic region being derived from the first tomographic image.

8. The optical coherence tomography observation apparatus according to claim 7, wherein the derived characteristic region is an image region where a change of a measurement value for each predetermined position interval exceeds a predetermined threshold value in the first tomographic image, and the image generator is configured to generate the second tomographic image with respect to the characteristic region.

9. The optical coherence tomography observation apparatus according to claim 1, wherein the image generator is further configured to generate a plurality of first tomographic images of the observation object at a predetermined time interval, and the image generator is configured to generate the second tomographic image when a change of a measurement value between two of the first tomographic images exceeds a predetermined threshold value.

10. The optical coherence tomography observation apparatus according to claim 1, wherein the first tomographic image is generated at a predetermined frame interval, and the image generator is configured to generate the second tomographic image at a predetermined time.

11. The optical coherence tomography observation apparatus according to claim 1, wherein the image generator is further configured to generate a plurality of first tomographic images of the observation object at a predetermined time interval, and the detector is configured to only calculate a correlation of a specific region in which a measurement value is approximately constant, the specific region being derived from the plurality of the first tomographic images.

12. The optical coherence tomography observation apparatus according to claim 1, further comprising:

an optical relative position changing unit that is configured to change an optical relative position of the observation object and the interference optical system, and a distance interval changing unit that is configured to change a distance interval when the optical relative position is changed based on information which indicates a definition supplied from an input, wherein the image generator generates the second tomographic image each time the optical relative position is changed.

13. The optical coherence tomography observation apparatus according to claim 1, wherein the detector comprises a correlation calculation unit and a relative position calculation unit, the correlation calculation unit being configured to calculate a correlation in a region in which a first tomographic image and a second tomographic image overlap each time a relative position of the second tomographic image with respect to the first tomographic image moves, and the relative position calculation unit being configured to determine a relative position of a second tomographic image with respect to a first tomographic image based on the calculated correlation.

14. A method for determining relative position, the method comprising:

providing an interference optical system that has function as an illumination optical system and as an observation optical system, the illumination optical system being configured to illuminate an observation object with an illumination light, the observation optical system being configured to observe a measurement light obtained from the observation object which is illuminated with the illumination light, a numerical aperture being changeable in at least one optical system of the illumination optical system and the observation optical system;

splitting incident light into reference light and illumination light in the interference optical system;

making the reference light and a measurement light interfere with each other in the interference optical system, the measurement light being obtained from an observation object which is illuminated with the illumination light;

detecting interference light generated from the interference by a light detection unit;

generating a first tomographic image which is within a first observation range of the observation object based on a first interference light, the first interference light being detected by the light detection unit in a state where the numerical aperture is set to a first numerical aperture;

generating second tomographic images which are within a second observation range of the observation object based on a second interference light, the second interference light being detected by the light detection unit in a state where the numerical aperture is set to a second numerical aperture which is larger than the first numerical aperture, the second observation range being smaller than the first observation range, a position of the second tomographic image in the observation object is moved in a depth direction of the observation object; and detecting a relative position for each of the first tomographic image and the second tomographic image at which a correlation of the first tomographic image and the second tomographic image becomes highest.

15. A non-transitory computer-readable storage medium storing a program for determining relative position of images, the program which comprises a storage unit, which stores a tomographic image of an observation object generated based on a detection result of an interference light by an interference, the interference being made by splitting incident light into reference light and illumination light, and making the reference light and a measurement light which is obtained from the observation object by illuminating the illumination light interference with each other, at an interference optical system that has a function of an illumination optical system which illuminates the observation object by the illumination light, and an observation optical system for observing the measurement light which is obtained from the observation object by illuminating the illumination light, to execute:

a step of storing information which indicates a first tomographic image which is within a first observation range of the observation object generated based on a detected first interference light in a state where one of a numerical aperture of the illumination optical system and the observation optical system is set to a first numerical aperture, a step of storing information which indicates second tomographic images which are within a second observation range of the observation object generated based on a detected second interference light in a state where one of the numerical aperture of the illumination optical system and the observation optical system is set to a second numerical aperture which is larger than the first numerical aperture, the second observation range being smaller than the first observation range, a position of the second tomographic image in the observation object is moved in a depth direction of the observation object, and a detection step of reading the information which indicates the first tomographic image and the information which indicates the second tomographic image from the storage unit, and detecting a relative position for each of the second tomographic image with respect to the first tomographic image, at which a correlation of the second tomographic image with the first tomographic image becomes highest.

\* \* \* \* \*